United States Patent [19]

Presty et al.

[11] Patent Number: 5,014,899
[45] Date of Patent: May 14, 1991

[54] SURGICAL STAPLING APPARATUS

[75] Inventors: Dominic F. Presty, Shelton; Thomas M. Tompkins, Trumbull, both of Conn.

[73] Assignee: United States Surgical Corporation, Norwalk, Conn.

[21] Appl. No.: 502,579

[22] Filed: Mar. 30, 1990

[51] Int. Cl.$^5$ .............................................. A61B 17/04
[52] U.S. Cl. ..................................... 227/180; 227/19; 227/151; 227/152
[58] Field of Search ............... 227/180, 175, 181, 176, 227/152, 151, 19

[56] References Cited

U.S. PATENT DOCUMENTS

| 3,078,465 | 2/1963 | Bobrov | 227/152 |
| 3,079,606 | 3/1963 | Bobrov et al. | |
| 3,490,675 | 1/1970 | Green et al. | |
| 3,499,591 | 3/1970 | Green | |
| 4,111,206 | 9/1978 | Vishnevsky et al. | 128/305 |
| 4,633,874 | 1/1987 | Chow et al. | 128/334 R |
| 4,915,100 | 4/1990 | Green | 227/176 |

Primary Examiner—Frank T. Yost
Assistant Examiner—John M. Husar
Attorney, Agent, or Firm—Thomas R. Bremer; Peter G. Dilworth; Rocco S. Barrese

[57] ABSTRACT

An improved apparatus for applying surgical fasteners to body tissue wherein the improvement comprises a resilient, deflectable arm which frictionally engages body tissue held between the anvil portion of the apparatus and the cartridge assembly of the apparatus. The deflectable arm exerts a biasing force on the tissue thereby holding the tissue in position to prevent misalignment.

18 Claims, 4 Drawing Sheets

Fig. 5
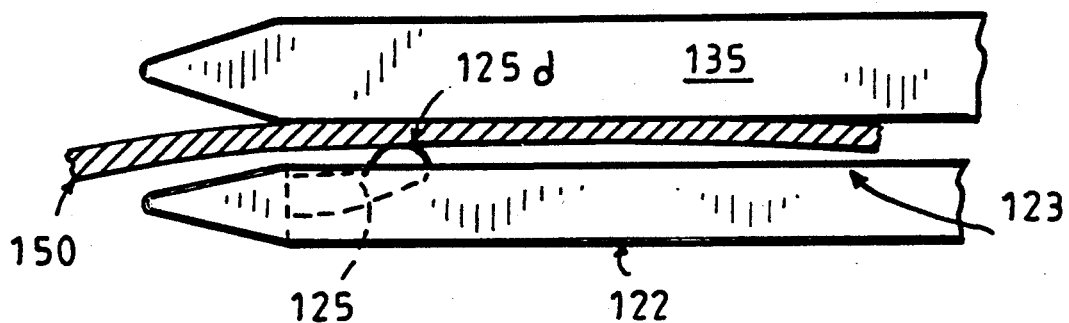
Fig. 6
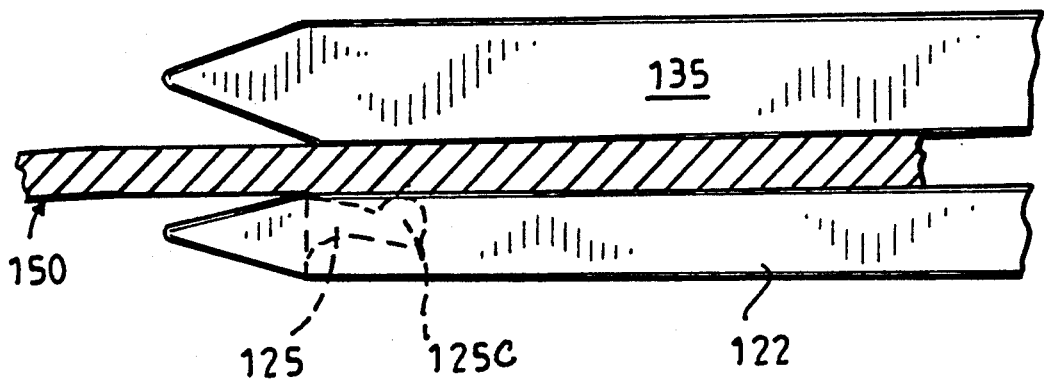
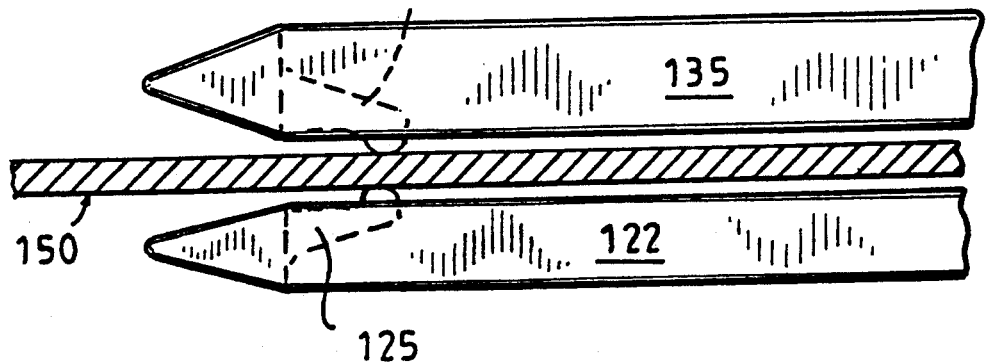
Fig. 7

SURGICAL STAPLING APPARATUS

BACKGROUND OF THE INVENTION

1. Field of the Invention

This invention relates to an apparatus for applying surgical fasteners, and more particularly to an apparatus for resection, transection and creation of anastomoses.

2. Background of the Art

Surgical fastening apparatus for resection, transection and creation of anastomoses are known in the art. For example, such apparatus are used for suturing gastric and intestinal walls with spaced parallel rows of longitudinally aligned surgical fasteners or staples. For example, U.S. Pat. No. 3,079,606 to Bobrov et al. discloses an instrument for suturing gastric and intestinal walls with metal staples by inserting the tips of the instrument through apertures in the walls of the organs to be sutured. The apparatus includes a two part frame with each part having a finger-like projection or fork. The forks are inserted respectively into the apertures in the walls of the organs to be sutured. The frame parts are hinged together with the body tissue held between the forks. When the instrument is actuated, or "fired", longitudinally moving cam bars contact staple drive members in one of the forks, thereby pushing the surgical staples through the body tissue and into an anvil in the opposite fork by which they are crimped closed. A knife blade between the cam bars creates an incision between the parallel rows of staples. It should be noted, however, that the knife blade is an optional feature, i.e. the instrument may be used to fasten body tissue without creating an incision between the rows of staples.

U.S. Pat. No. 3,490,675 to Green et al. discloses an improvement on the instrument discussed above, whereby a double row of staples is placed on each side of the incision.

A further improvement in this type of instrument is disclosed in U.S. Pat. No. 3,499,591 to Green, which incorporates an improved structure for the staple carrying cartridge, the pusher assembly which includes the cam bars and the knife, and the staple drive members.

Generally, the above mentioned instruments are successfully used in abdominal, gynecological, pediatric and thoracic surgery for resection, transection, and creation of anastomoses. Surgical fastener applying apparatus can be used to apply metal staples, which are crimped in the anvil portion of the apparatus, or bioabsorbable fasteners, such as two-part fasteners having a fastener portion and a retainer which interlocks therewith upon firing of the instrument. In any such instrument it is important to maintain proper alignments: alignment of the jaws of the instrument, and alignment of the tissue held between the jaws.

Alignment of the instrument jaws insures that the surgical fasteners are properly closed. In the case of metal staples, the staples are closed when their legs are crimped in corresponding depressions in the anvil. With respect to the two-part fasteners, the fastener portions must be properly aligned with the corresponding retainer portions in the anvil assembly so that closure, or interlocking can be achieved.

Tissue alignment insures that the instrument operates on the proper area of tissue. Such instruments, of course, are employed on various thicknesses of tissue. However, thinner tissue may have a tendency to become misaligned by shifting within the closed instrument. The possibility of such misalignment of tissue is increased by the presence of body fluids, such as blood, which tend to make the tissue slippery. On the other hand, an instrument whose jaws close firmly on thin tissue to prevent its misalignment might pinch the tissue, particularly thicker tissue.

One method which has been employed to preserve alignment of the instrument jaws is to use positioning buttons or projections on the lateral edges of the cartridge. These projections guide the anvil portion into proper alignment with the staple cartridge when the jaws of the instrument are closed. Under some circumstances, however, such projections can act as pinch points for tissue.

An improvement has now been developed for maintaining alignment of both the jaws of the instrument and the tissue between the jaws, without causing pinching of the tissue. Furthermore, various tissue thicknesses are automatically accommodated between the instrument jaws.

SUMMARY OF THE INVENTION

An apparatus for applying surgical fasteners to body tissue is provided herein. The apparatus comprises: a first means for carrying a plurality of surgical fasteners; a second means adapted for closure of a plurality of the fasteners; and a means connected to the second means having a raised portion movable relative to the first means when the first and second means are positioned in adjacent relation with the tissue gripped therebetween. The raised portion engages the tissue with force sufficient to maintain respective alignment of the tissue and said first and second means.

The first means can include a first frame having a distally projecting, finger-like member for carrying a fastener holding cartridge and a fastener holding cartridge including at least two parallel rows of staple carrying slots arrayed in longitudinally extending lines, and including a longitudinally extending knife slot laterally intermediate said rows of staple carrying slots. The second means can include a second frame having a distally projecting finger-like member for carrying an anvil assembly. The first and second frames are hingedly securable to each other such that their respective finger-like members form jaws for closing on body tissue positioned therebetween. The anvil assembly has means for effecting closure of the surgical fasteners and also has a knife slot aligned with the knife slot of the staple carrying cartridge so as to permit a knife blade to simultaneously move longitudinally along both slots. The apparatus includes means for ejecting said surgical fasteners from the fastener carrying slots into contact with the anvil assembly to effect closure thereof.

The means connected to the second means and having a raised portion is a resiliently deflectable arm having a tissue engaging surface, said tissue engaging surface exerting a biasing force on tissue located between the closed jaws of the apparatus for frictionally holding said tissue in alignment.

The deflectable arm is mounted on the second frame at the distal end of the anvil knife slot, within which it is movable. The deflectable arm is preferably constructed of a strong, resilient polymeric material.

BRIEF DESCRIPTION OF THE DRAWINGS

Preferred embodiments of the invention are described hereinbelow, wherein:

FIGS. 5 and 6 illustrate the operation of the resilient deflectable arm in maintaining tissue alignment.

FIG. 7 illustrates an alternative embodiment employing two deflectable arms.

DETAILED DESCRIPTION OF THE PREFERRED EMBODIMENTS

Figure 1:
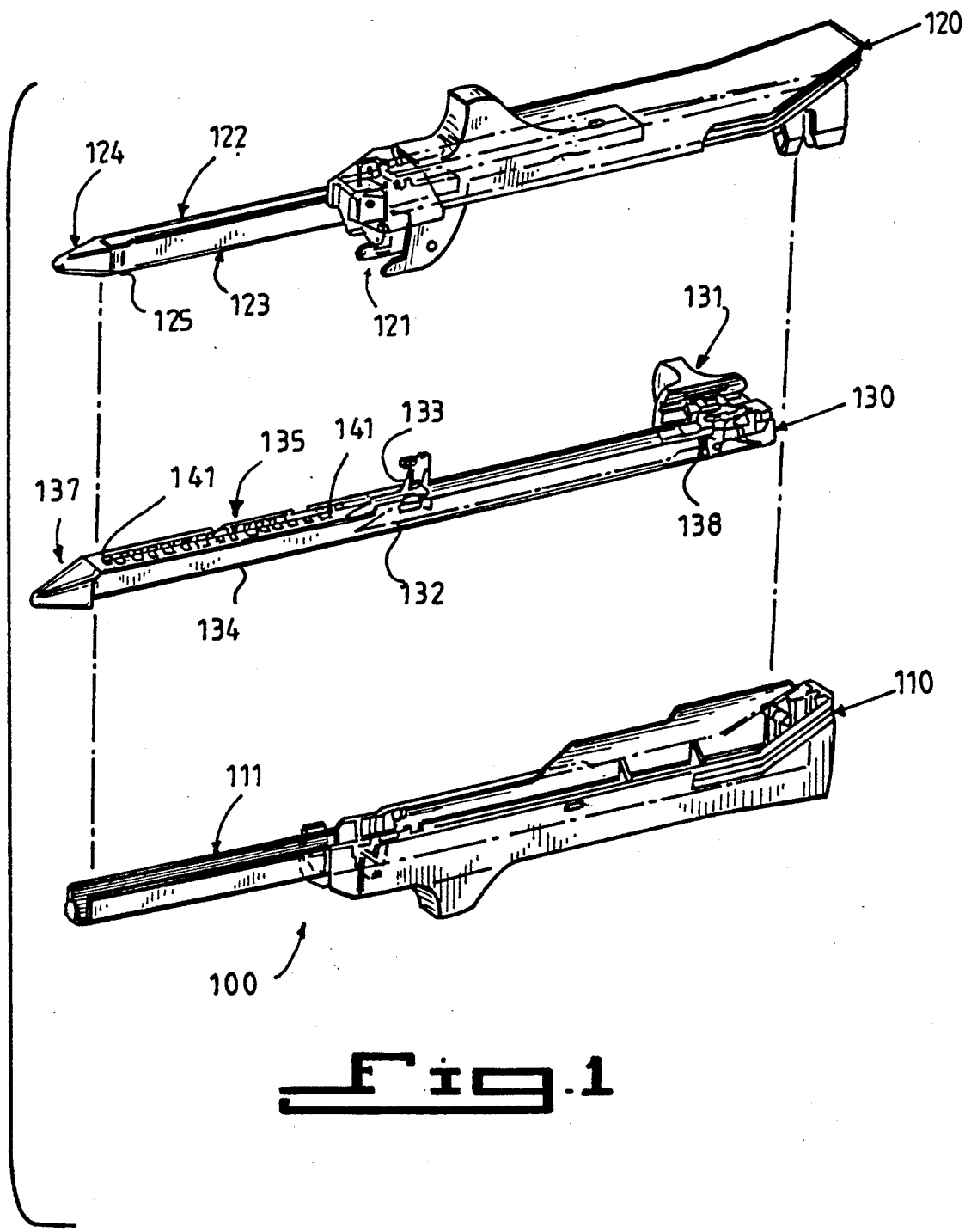
FIG. 1 is a perspective view with parts separated of a surgical stapling apparatus.

Referring to FIG. 1, the surgical stapling apparatus 100 of the present invention comprises a first frame 110 having a distal finger-like projection 111 for holding a cartridge assembly. A second frame 120 has a pair of hinge plates 121 for hingedly connecting to the first frame 110, and a distal finger-like projection 122 for carrying an anvil assembly 123. The anvil assembly 123 is formed of a plate with indentations or depressions 128 as shown more clearly in FIG. 4, for crimping the legs of metal staples. Alternatively, the anvil assembly may include means for holding rows of retainer portions of two-part surgical fasteners to facilitate mutual engagement of the fastener and retainer portions of the two-part fasteners. Tip 124 allows distal projection 122 to be more easily positioned in body tissue. The resilient deflectable arm 125 is preferably attached to tip 124. Deflectable arm 125 may be formed integral with the tip 124, or it may be in the form of a separate attachment.

Figure 2:
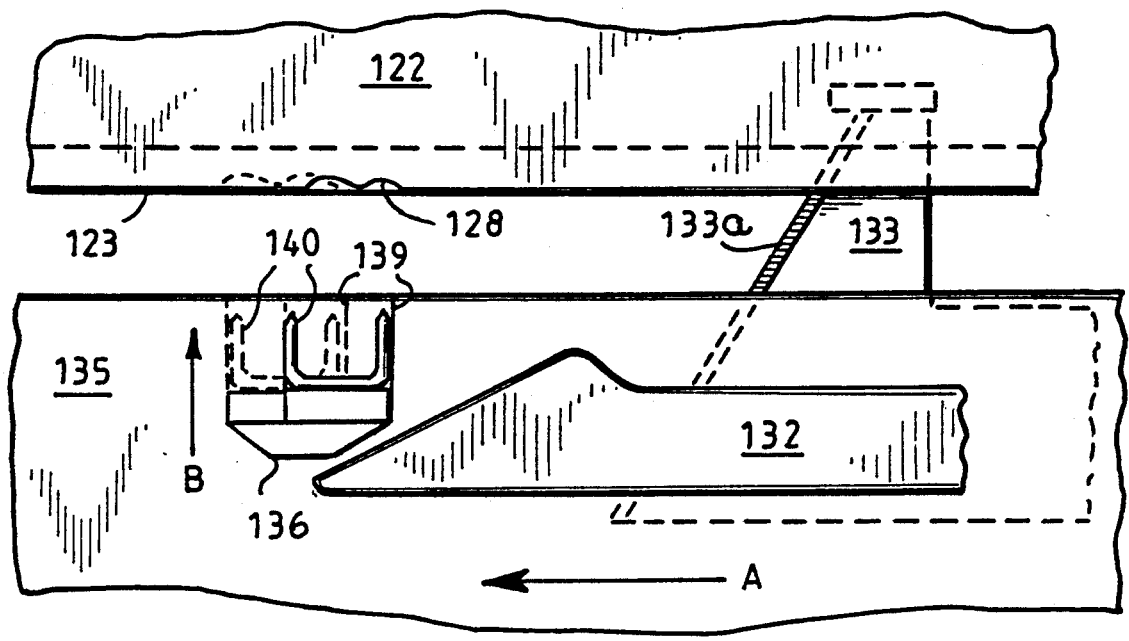
FIG. 2 is an elevational view illustrating a portion of the cartridge assembly.

Actuating assembly 130 for driving the surgical fasteners is a replaceable insert which includes a pusher assembly having a thrust knob 131, cam bars 132, and knife blade 133. The actuating assembly or insert 130 further includes a stationary carrier 134 for holding cartridge assembly 135. Tip 137 at the distal end of the cartridge assembly facilitates positioning body tissue for fastening. Referring also to FIG. 2, cartridge assembly 135 includes pusher members 136 for pushing surgical fasteners out from their respective slots and into contact with the anvil for closure. Cam bars 132 and knife 133 are mounted at their proximal ends to cam bar retainer 138, which is connected to the thrust knob 131 and which provides a means for transferring manually applied force from the thrust knob 131 to the cam bars 132.

In operation the insert 130 is loaded into the first frame 110, and the instrument is then assembled such that the body tissue to be operated upon is located between the cartridge assembly 135 and the anvil assembly 123. The knife 133 is positioned such that it can simultaneously move along slot 126 (see FIG. 4) in the anvil and slot 141 (FIG. 1) in the cartridge assembly. The instrument is then fired by the surgeon's pressing forward (i.e. distally) on the thrust knob 131.

Referring again to FIG. 2, the cam bars 132 and knife 133 are then moved distally and longitudinally along the instrument in the direction indicated by arrow A. The knife 133 creates an incision in the body tissue (not shown) by means of its distal cutting edge 133a, and the cam bars 132 drive the fastener pushers 136 in a direction indicated by arrow B, which is transverse to that of the longitudinal axis of the instrument. The pushers 136, in turn, drive the fasteners 140 out of their slots 139 and into the depressions 128 in the anvil plate for crimping, thereby fastening the tissue on both sides of the incision. When the operation is completed the used replaceable insert 130 can be disposed, and a new one installed in the apparatus.

Figure 3:
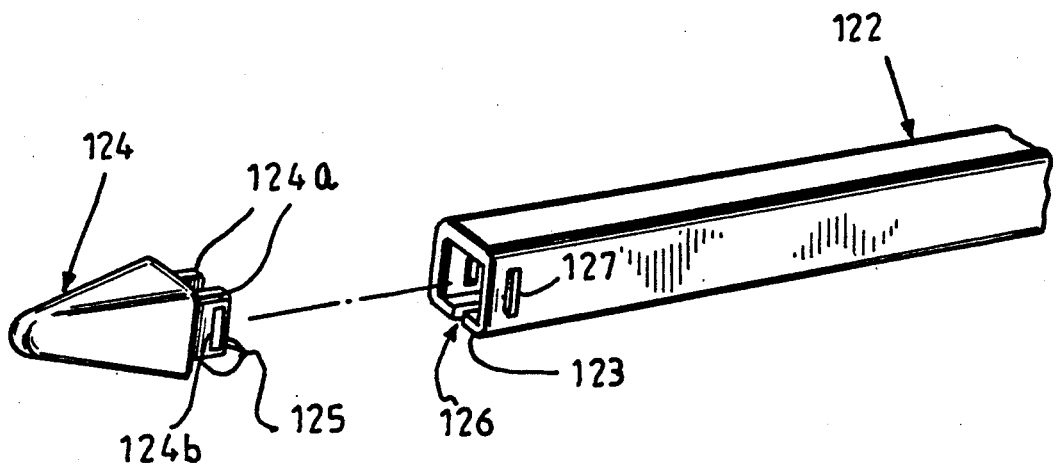
FIG. 3 is an exploded perspective view illustrating the anvil tip including the resilient deflectable arm of the present invention.

FIG. 3 illustrates the anvil tip 124 having prongs 124a and detents 124b on the outer sides of the prongs. The detents 124b are for engaging side slots 127 in the distal projection 122. Distal projection 122 carries an anvil assembly which can simply comprise an anvil plate 123a with depressions 128 for crimping the legs of staples. Alternatively, the anvil assembly can house the retainer portions of two-part bioabsorbable surgical fasteners and means for releasably holding them until they are engaged with their respective fastener portions.

Figure 4:
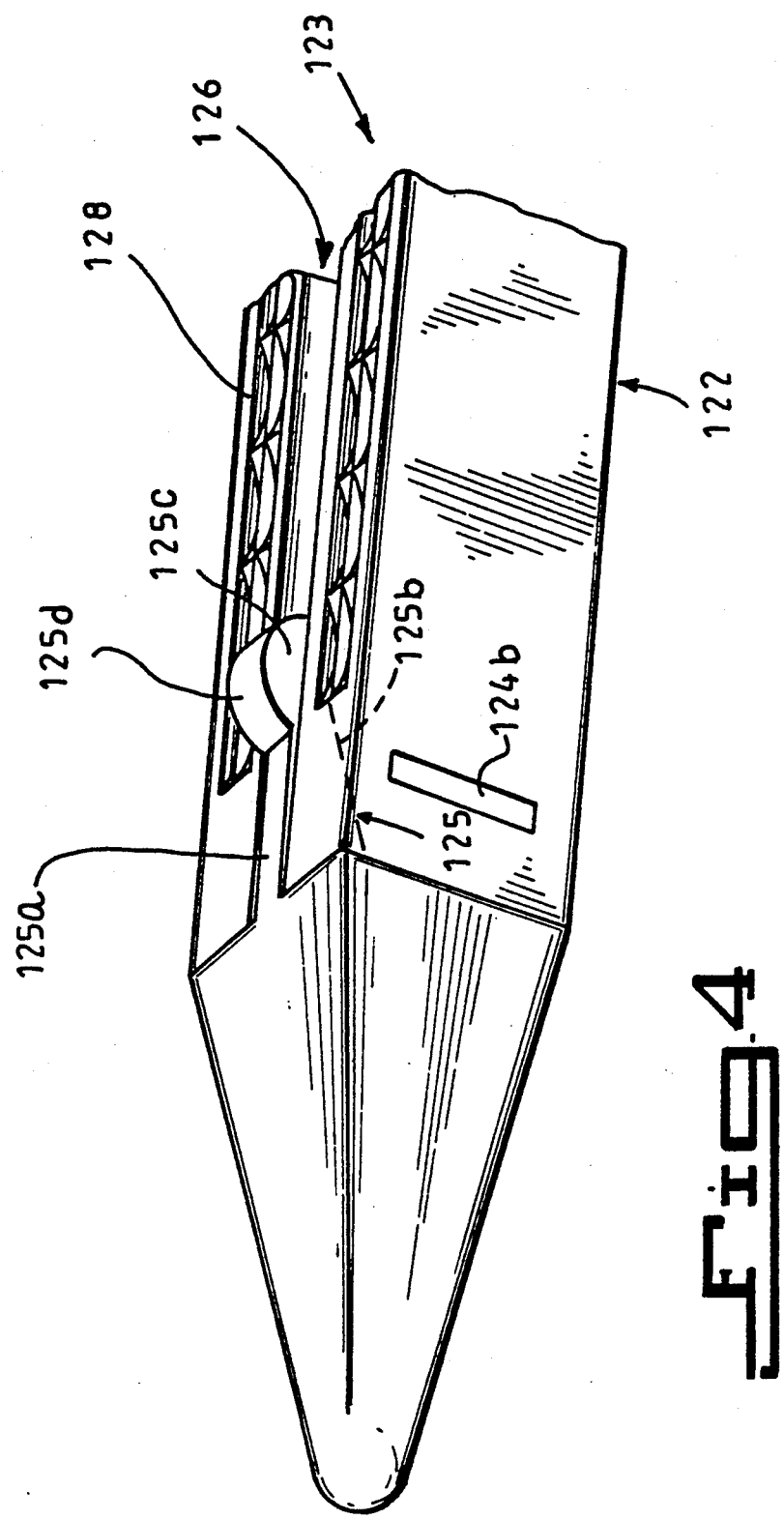
FIG. 4 is a perspective view illustrating the resilient deflectable arm in position within the anvil knife slot.

Referring now to FIGS. 3 and 4, the resilient, deflectable arm 125 projects proximally from tip 124 and is configured and dimensioned to fit within knife slot 126 at the distal end thereof. The deflectable arm 125 has a surface 125a substantially flush with the surface of the anvil plate 123. Projection 125c at the proximal end of arm 125 extends beyond the anvil surface into the gap between the anvil 123 and the cartridge assembly. Curved tissue engaging surface 125d of the projection 125c defines a substantially semicircular shape. The semicircular or arcuate configuration of the tissue engaging surface 125d provides a significant advantage: as projection 125c of the deflectable arm engages the tissue and moves away from the aforementioned gap, the tissue engaging surface 125d will move easily relative to the tissue while maintaining engagement with it. Thus, projection 125c engages and holds the tissue without grabbing or binding it. Surface 125b is preferably inclined with respect to surface 125a when deflectable arm 125 is in its initial, unloaded position. The arm 125 is constructed of a resilient material to enable it to be deflected by pressure on the tissue engaging surface 125d such that projection 125c is resiliently deflectable in the lateral direction relative to the tissue.

FIGS. 5 and 6 illustrate the operation of the deflectable arm 125. When relatively thin body tissue 150 is located between the cartridge assembly 135 and the anvil 123, as illustrated in FIG. 5, the tissue engaging surface 125d frictionally engages body tissue 150 and exerts a biasing force on the tissue 150 to prevent the tissue 150 from moving out of alignment. When the body tissue 150 is relatively thick, as illustrated in FIG. 6, the arm 125 resiliently deflects such that the projection 125c moves out of the gap area between the anvil 123 and the cartridge assembly 135, thereby avoiding pinching or damaging of the tissue 150.

The deflectable arm 125 also helps maintain alignment between the cartridge assembly 135 and the anvil assembly 123. The biasing force exerted by the arm 125 is aligned with the knife slot 141 of the cartridge assembly, thereby creating interference which inhibits lateral misalignment of the cartridge assembly and the anvil assembly. Although the above description and accompanying figures show the deflectable arm 125 associated with anvil assembly 123, it is also contemplated that the deflectable arm may be associated with cartridge assembly 135, particularly when the surgical fastening apparatus does not include a knife. A further embodiment of the present invention would include multiple deflectable arms 125, e.g., a pair of cooperating deflectable arms in opposing relationship to each other at the distal end of the apparatus, one arm being associated with the anvil assembly 123 and the other arm being associated with cartridge assembly 135. An embodiment employing two deflectable arms is illustrated in FIG. 7.

The arm 125 can be constructed from any suitable polymeric material having the appropriate strength and resiliency for its purpose, e.g. Lexan ® (General Electric). Preferably, the arm 125 and the tip 124 are integrally constructed by injection molding.

What is claimed is:

1. Apparatus for applying surgical fasteners to body tissue, which comprises:

first means for carrying a plurality of surgical fasteners;

second means adapted for effecting closure of a plurality of said fasteners; and, at least one of said second fastener closure means and said first fastener carrying means having a resilient deflectable member with a raised portion movable relative to the tissue when said first and second means are positioned in adjacent relation with the tissue gripped therebetween, said raised portion engaging the tissue with force sufficient to maintain alignment of the tissue, and said resilient deflectable member being located within the periphery of at least one of said first or second means.

2. Apparatus for applying surgical fasteners to tissue, which comprises:

(a) at least a pair of jaws adapted for reception of tissue therebetween for applying surgical fasteners to the tissue;

(b) means on at least one of said jaws for carrying a plurality of surgical fasteners;

(c) means correspondingly positioned on the other of said jaws for effecting closure of a plurality of said surgical fasteners; and, (d) means connected to at least one of said jaws and including a deflectable raised portion movable with respect to, and to a position at least partially within, a slot in said at least one jaw and extending toward the other of said jaws for engaging the tissue when the jaws are closed in preparation for applying fasteners to the tissue, said raised portion being laterally movable relative to said tissue such that said raised portion exerts sufficient force against the tissue to secure the tissue firmly with respect to said jaws.

3. An apparatus for applying surgical fasteners which comprises:

first frame including a distally projecting, finger-like member for carrying a fastener holding cartridge;

second frame including a distally projecting finger-like member for carrying an anvil assembly, said first and second frames being hingedly securable to each other such that their respective finger-like members form jaws for closing on body tissue positioned therebetween;

fastener holding cartridge including at least two parallel rows of fastener carrying slots arrayed in longitudinally extending lines, and including a longitudinally extending knife slot laterally intermediate said rows of staple carrying slots;

an anvil assembly having means for effecting closure of the surgical fasteners and having a knife slot aligned with said knife slot of the staple carrying cartridge to permit a knife blade to simultaneously move longitudinally along both the anvil assembly knife slot and the cartridge assembly knife slot;

means for ejecting said surgical fasteners from the fastener carrying slots into the anvil assembly to effect closure thereof; and, at least one deflectable arm having a tissue engaging surface, said tissue engaging surface exerting a biasing force on tissue located between the closed jaws of the apparatus for frictionally holding said tissue in alignment, and said deflectable arm being in substantial longitudinal alignment with said knife slot.

4. The apparatus of claim 3 wherein said arm is constructed from a resilient material.

5. The apparatus of claim 4 wherein said resilient material is a polymeric material.

6. The apparatus of claim 3 wherein said tissue engaging surface is curved.

7. The apparatus of claim 6 wherein the deflectable arm includes a projection located at the proximal end of said arm, said projection having a raised arcuate shape defining said tissue engaging surface, and said projection being resiliently movable between a first position in which the projection is located at least partially in the gap between the anvil assembly and the cartridge assembly, and a second position in which said projection is located substantially within said knife slot of the anvil assembly.

8. The apparatus of claim 3 wherein the distal end of said deflectable arm is mounted to the second frame.

9. The apparatus according to claim 8 wherein said deflectable arm is carried by a tip member connected to the distal portion of said finger-like member of said second frame.

10. The apparatus according to claim 9 wherein said raised arcuate portion has a semi-circular configuration and said deflectable arm formed integrally with said tip member.

11. The apparatus according to claim 10 wherein said tip member is fabricated of a polymeric material.

12. The apparatus of claim 4 wherein said deflectable arm is configured and dimensioned to move within the anvil assembly knife slot at the distal end thereof.

13. The apparatus of claim 3 wherein said surgical fasteners are staples, said staples being crimped by corresponding depressions in the anvil assembly surface when the apparatus is fired.

14. The apparatus of claim 3 wherein said apparatus comprises two deflectable arms, one of said two deflectable arms being associated with the fastener holding cartridge and the other of said two deflectable arms being associated with the anvil assembly.

15. The apparatus of claim 14 wherein said two deflectable arms cooperate in opposing relation to each other to position tissue between the fastener holding cartridge and the anvil assembly.

16. The apparatus of claims 1 or 2 wherein said raised portion comprises a projection located on a resilient arm and having a tissue engaging surface.

17. The apparatus of claim 16 wherein the projection is located at the proximal end of said resilient arm being mounted to the means for effecting closure of the fasteners.

18. The apparatus of claim 16 wherein said tissue engaging surface has an arcuate configuration.

* * * * *

UNITED STATES PATENT AND TRADEMARK OFFICE
CERTIFICATE OF CORRECTION

PATENT NO. : 5,014,899

DATED : May 14, 1991

INVENTOR(S) : Presty et al

It is certified that error appears in the above-identified patent and that said Letters Patent is hereby corrected as shown below:

In column 4, line 10, change "123a" to --123--.

Signed and Sealed this

Nineteenth Day of January, 1993

Attest:

DOUGLAS B. COMER

Attesting Officer

Acting Commissioner of Patents and Trademarks